(12) United States Patent
Stancovski et al.

(10) Patent No.: US 7,964,084 B2
(45) Date of Patent: Jun. 21, 2011

(54) METHODS AND APPARATUS FOR THE SYNTHESIS OF USEFUL COMPOUNDS

(75) Inventors: Victor Stancovski, Groton, CT (US); Steven Lawrence Suib, Storrs, CT (US); Boxun Hu, Storrs, CT (US)

(73) Assignees: Catelectric Corp., Hartford, CT (US); The University of Connecticut, Farmington, CT (US)

(*) Notice: Subject to any disclaimer, the term of this patent is extended or adjusted under 35 U.S.C. 154(b) by 357 days.

(21) Appl. No.: 12/284,337

(22) Filed: Sep. 18, 2008

(65) Prior Publication Data
US 2009/0134037 A1 May 28, 2009

Related U.S. Application Data

(60) Provisional application No. 60/994,854, filed on Sep. 20, 2007.

(51) Int. Cl.
*C25B 15/08* (2006.01)
(52) U.S. Cl. ........ 205/337; 205/341; 205/334; 205/413; 205/422
(58) Field of Classification Search ............... 205/334, 205/337, 341, 413, 422; 502/128; 526/129
See application file for complete search history.

(56) References Cited

U.S. PATENT DOCUMENTS

| | | | |
|---|---|---|---|
| 2,908,734 A | 10/1959 | Cottle | |
| 4,233,132 A | 11/1980 | Carr et al. | |
| 4,272,336 A | 6/1981 | Vayenas et al. | |
| 4,318,708 A | 3/1982 | Hogberg | |
| 4,329,208 A | 5/1982 | Vayenas et al. | |
| 4,463,065 A | 7/1984 | Hegedus et al. | |
| 4,512,964 A | 4/1985 | Vayenas et al. | |
| 4,643,806 A | 2/1987 | Hegedus et al. | |
| 4,673,473 A | 6/1987 | Ang et al. | |
| 5,006,425 A | 4/1991 | Takabayashi | |
| 5,232,882 A | 8/1993 | Yoshimoto et al. | |
| 6,194,623 B1 | 2/2001 | Frenzel et al. | |
| 6,214,195 B1 | 4/2001 | Yadav et al. | |
| 6,267,864 B1 | 7/2001 | Yadav et al. | |
| 6,387,228 B1 | 5/2002 | Maget | |
| 6,562,495 B2 | 5/2003 | Yadav et al. | |
| 6,723,886 B2 | 4/2004 | Allison et al. | |
| 6,833,272 B1 | 12/2004 | Binder et al. | |
| 6,852,865 B2 | 2/2005 | Coates et al. | |
| 6,966,178 B2* | 11/2005 | Saito et al. | |
| 7,001,500 B2 | 2/2006 | Bors et al. | |
| 7,087,147 B2 | 8/2006 | Bors et al. | |
| 7,325,392 B2* | 2/2008 | Stancovski et al. ........... 60/275 |
| 2001/0000889 A1 | 5/2001 | Yadav et al. | |
| 2002/0014417 A1 | 2/2002 | Kuehnle et al. | |
| 2002/0045076 A1 | 4/2002 | Dieckmann et al. | |
| 2002/0124551 A1 | 9/2002 | Birkhofer et al. | |
| 2002/0128506 A1 | 9/2002 | Suib et al. | |
| 2003/0010629 A1 | 1/2003 | St. Pierre et al. | |
| 2003/0118861 A1 | 6/2003 | Heimann et al. | |
| 2004/0007475 A1 | 1/2004 | Stancovski et al. | |
| 2005/0027431 A1* | 2/2005 | Todoroki et al. | |
| 2005/0202660 A1 | 9/2005 | Cohen et al. | |
| 2005/0227381 A1 | 10/2005 | Cao et al. | |
| 2005/0244682 A1 | 11/2005 | Meacham | |
| 2006/0235091 A1 | 10/2006 | Olah et al. | |
| 2007/0095673 A1 | 5/2007 | Stancovski et al. | |
| 2007/0161717 A1 | 7/2007 | Hu et al. | |
| 2007/0246364 A1 | 10/2007 | Amlani et al. | |
| 2007/0254969 A1 | 11/2007 | Olah et al. | |
| 2007/0255039 A1 | 11/2007 | Coates et al. | |
| 2009/0101516 A1* | 4/2009 | Suib et al. ............. 205/338 |

FOREIGN PATENT DOCUMENTS

| | | |
|---|---|---|
| CN | 1280105 | 1/2001 |
| DE | 199 31 007 | 1/2001 |
| EP | 0 480 116 | 4/1992 |
| EP | 0 665 047 | 8/1995 |
| EP | 0 903 476 | 3/1999 |
| WO | 95/20556 | 8/1995 |

OTHER PUBLICATIONS

Hara, et al. "Electrocatalytic Fischer-Tropsch Reactions. Formation of Hydrocarbons and Oxygen-Containing Compounds from CO on a Pt Gas Diffusion Electrode," Bulletin of the Chemical Society of Japan vol. 70 (1997), No. 4 pp. 745-754.(abstract).

Larry L. Miller, et al., "Electrocatalytic Hydrogenation of Aromatic Compounds," The Journal of Organic Chemistry, 1978, vol. 43 No. 10, pp. 2059-2061.

"Optimisation of Solid State Electrochemical Processes for Hydrocarbon Oxidation (OSSEP)," European Science Foundation, Oct. 2000, 8 pages.

S.L. Douvartzides, et al., "Electrochemically Promoted Catalysis; The Case of Ethanol Oxidation over Pt," Journal of Catalysis 211, pp. 521-529, 2002.

D. Tsiplakides et al., "Introduction to Electrochemical Promotion, Non-faradaic Electrochemical Modification of Catalytic Activity (*NEMCA effect*)," J. Electrochemical Soc., 144(6), 272-288, 1997 (25 pages). *Modern Aspects of Electrochemistry No. 29*, "The Electrochemical Activation of Catalytic Reactions", Constantinos G. Vayenas et al., pp. 57-202, Plenum Press—New York and London, 1996.

T.J. Schmidt et al., "Oxygen Electrocatalysis in Alkaline Electrolyte: Pt(*hkl*), Au(*hkl*) and the Effect of PD-Modification," Electrochimica Acta 47, pp. 3765-3776, 2002.

Gianfranco Pacchioni et al., "Electric Field Effects in Heterogeneous Catalysis," Journal of Molecular Catalysis A: Chemical 119, pp. 263-273, 1997.

Ian S. Metcalfe, "Electrochemical Promotion of Catalysis, II: The Role of a Stable Spillover Species and Prediction of Reaction Rate Modification," Journal of Catalysis 199, pp. 259-272, 2001.

G. Fóti et al., "Transient Behavior of Electrochemical Promotion of Gas-Phase Catalytic Reactions," Journal of Electroanalytical Chemistry 532, pp. 191-199, 2002.

S. Bebelis et al., "Electrochemical Activation of Catalytic Reactions Using Anionic, Cationic and Mixed Conductors," Solid State Ionics 129, pp. 33-46, 2000.

(Continued)

*Primary Examiner* — Bruce F Bell
(74) *Attorney, Agent, or Firm* — Lipsitz & McAllister, LlC

(57) ABSTRACT

The present invention relates to methods and apparatus for activation of a low reactivity, non-polar chemical compound. In one example embodiment, the method comprises introducing the low reactivity chemical compound to a catalyst. At least one of (a) an oxidizing agent or a reducing agent and (b) a polar compound is provided to the catalyst and the chemical compound. An alternating current is applied to the catalyst to produce an activation reaction in the chemical compound. This activation reaction produces a useful product.

34 Claims, 10 Drawing Sheets

OTHER PUBLICATIONS

Soonho Kim et al., "Solid Electrolyte Aided Studies of NO—CO Reaction on Pd," Solid State Ionics 136-137, pp. 693-697, 2000.

G. Fóti et al., "Electrochemical Promotion of $IrO_2$ Catalyst for the Gas-Phase Combustion of Ethylene," publisher and publication date unknown (1 page).

Seetharaman Sridhar, et al. "Effect of Oxygen-Containing Species on the Iimpedance of the Pt/YSZ Interface" Solid State Ionics 100 (1997) 17-22.

Seetharaman Sridhar, et al. "Transient and Permanent Effects of Direct Current on Oxygen Transfer across YSZ-Electrode Interfaces" Journal of the Electrochemical Society, vol. 144; No. 7, Jul. 1997, 2479-2485.

Victor Stancovski et al., "Thermodynamic Stability and Interfacial Impedance of Solid-Electrolyte Cells with Noble-Metal Electrodes" Journal of Electroceramics 3:3, pp. 279-299; 1999.

"Corrosion of Materials"; Applications of Impedance Spectroscopy p. 260-267 (undated).

Ch. Karavasilis et al., "Non-Faradaic Electrochemical Modification of Catalytic Activity—X. Ethylene Epoxidation on AG Deposited on Stabilized $ZrO_2$ in the Presence of Chlorine Moderators"—Journal of Catalysis 160, pp. 190-204, (1996).

Michael Stoukides et al., "The Effect of Electrochemical Oxygen Pumping on the Rate and Selectivity of Ethylene Oxidation on Polycrystalline Silver", Journal of Catalysis 70, pp. 137-146 (1981).

Jikang Yuan et al., "Spontaneous Formation of Inorganic Paper-Like Materials", Advanced Materials 2004, 16, No. 19 Oct. 4, pp. 1729-1732.

F. Richard Keene, "Thermodynamic, Kinetic, and Product Considerations in Carbon Dioxide Reactivity", Department of Chemistry and Biochemistry, James Cook University of North Queensland, Townsville, Australia, Chapter One—pp. 1-18 (undated).

A. Katsaounis, "Electrochemical Promotion of Catalysis (EPOC) Perspectives for Application to Gas Emissions Treatment", Global NEST Journal 2008, pp. 1-11.

Prachi Patel-Predd, "Carbon-Dioxide Plastic Gets Funding", MIT Technology Review (2007), one page.

"Devices Uses Solar Energy to Convert Carbon Dioxide into Fuel", Physorg.com, pp. 1-2 (undated).

Toshiyasu Sakakura, et al., "Transformation of Carbon Dioxide" Chem. Rev. 2007, 107, pp. 2365-2387.

Aimin Huang, et al., "CO2 Reforming of CH4 by Atmospheric Pressure ac Discharge Plasmas" Journal of Catalysis, 189, pp. 349-359 (2000).

Steven L. Suib, et al., "A Direct, Continuous, Low-Power Catalytic Conversion of Methane to Higher Hydrocarbons via Microwave Plasmas" Journal of Catalysis, 139, pp. 383-391 (1993).

K. Ogura, et al., "Reduction of $CO_2$ to Ethylene at Three-Phase Interface Effects of Electrode Substrate and Catalytic Coating", Journal of the Electrochemical Society, 152 12), pp. D213-D219 (2005).

Michael Schwartz, et al., "Fischer-Tropsch Electrochemical $CO_2$ Reduction to Fuels and Chemicals", Journal of the Electrochemical Society, vol. 141 No. 11, Nov. 1994, pp. 3119-3127.

Shigeki Furukawa, et al., "Isolation of Oxygen Formed during Catalytic Reduction of Carbon Dioxide Using a Solid Electrolyte Membrane" Energy & Fuels, 1999, 13, pp. 1074-1081.

M. Gattrell, et al., "A Review of the Aqueous Electrochemical Reduction of $CO_2$ to Hydrocarbons at Copper," Journal of Electroanalytical Chemistry, 594,(2006) pp. 1-19.

G. R. Dey, et al., "Gas-Phase and On-Surface Chemical Reduction of CO2 to HCHO and CO Under Dielectric Barrier Discharge," Plasma Chem Plasma Process (2006), 26, pp. 495-505.

"Research Proposal for the Enhancement of Fischer-Topsch Process", Proof of concept performed at the University of Connecticut (2005-2006) pp. 3-15.

Ali, et al., "Selective Formation of HCO2− and C2 O42− in Electrochemical Reduction of CO2 Catalyzed by Mono- and Di-Nuclear Ruthenium Complexes," Chem. Commun., 1998, pp. 249-250.

J. Llorca, et al., "On the Reaction between Carbon Dioxide, Ethylene, and Water over Supported Platinum-Tin Catalysts. A Combined Drift-Mass Spectrometry Study." Journal of Catalysis, 197, pp. 220-223 (2001.

Yoshie Kitayama, et al., "Catalytic Reduction of Carbon Dioxide on Ni—Cu Alloys." Energy, vol. 22 No. 2/3, pp. 177-182 (1997).

Koji Tanaka, et al., "Multi-electron reduction of CO2 via Ru—CO2, -C(O)OH, -CO, -CHO, and -CHO2OH Species," Coordination Chemistry Reviews, 226, (2002) pp. 211-218.

Xiaolong Yin, et al., "Recent Developments in the Activation of Carbon Dioxide by Metal Complexes." Coordination Chemistry reviews, 181, (1999) pp. 27-59.

Xiao-Guang Zhang, et al., "Activation of O2 and CO2 by PtO+: The Thermochemistry of $PtO_2+$" J. Phys. Chem. A, 2003, 107, pp. 8915-8922.

C.G. Vayenas, et al., "Dependence of Catalytic Rates on Catalyst Work Function," Letters to Nature, vol. 343, pp. 625-627 (Feb. 15, 1990).

Bruce A. Parkinson, et al., "Photoelectrochemical Pumping of Enzymatic CO2 Reduction," Letters to Nature, vol. 309, pp. 148-149 (May 10, 1984).

Daniel Mandler, et al., "Effective Photoreduction of $CO_2/HCO_{3-}$ to Formate Using Visible Light," J. Am. Chem. Soc., 1987, 109, pp. 7884-7885.

Steven L. Suib, et al., "Efficient Catalytic Plasma Activation of $CO_2$, NO, and $H_2O$," J. Phys. Chem. B., 1998, 102, pp. 9661-9666.

J. Zhang, et al., "Stabilization of Platinum Oxygen-Reduction Electrocatalysts Using Gold Clusters," Science Magazine, vol. 315, pp. 220-222, Jan. 12, 2007.

Matthew W. Kanan, et al., "In Situ Formation of an Oxygen-Evolving Catalyst in Neutral Water Containing Phosphate and $Co^{2+}$," Science Magazine, vol. 321, pp. 1072-1075, Aug. 22, 2008.

C. Pliangos, et al, "Electrochemical Promotion of the $NO_x$ Reduction over Pt, Pd and Rh Catalysts", University of Patras, Department of Chemical Engineering, Greece, 2 pages (undated).

S.G. Neophytides, et al, "Non-Faradaic Electrochemical Modification of the Catalytic Activity of Pt for $H_2$ Oxidation in Aqueous Alkaline Media", J. Phys. Chem., 1996, vol. 100 No. 35, p. 14803 (Abstract).

"New Electrochemically Smart Catalysts for Hazardous Waste Management and Development of Capillary Electrophoresis for Analysis of their Products" Lamar University (undated).

K. Ogura, et al, "Reduction of $CO_2$ to Ethylene at Three-Phase Interface Effects of Electrode Substrate and Catalytic Coating", Journal of Electrochemical Society, 152 (12), pp. D213-D219 (2005).

Nobuhito Imanaka, et al, "Total Nitrogen Oxides Gas Sensor Based on Solid Electrolytes with Refractory Oxide-Based Auxiliary Electrode", Journal of Electrochemical Society, 151 (5), pp. H113-H116 (2004).

V. Stamenkovic, et al, "Surface Segregation Effects in Electrocatalysis: Kinetics of Oxygen Reduction Reaction on Polycrystalline $Pt_3Ni$ Alloy Surfaces", Journal of Electroanalytical Chemistry, 554-555 (2003), pp. 191-199.

V. Stamenkovic, et al, "Surface Composition Effects in Electrocatalysis: Kinetics of Oxygen Reduction on Well-Defined $Pt_3Ni$ and $Pt_3Co$ Alloy Surfaces", J. Phys. Chem. B, 2002, vol. 106, pp. 11970-11979.

Atanu Dutta, et al, "Study of YSZ-Based Electrochemical Sensors with $WO_3$ Electrodes in $NO_2$ and CO Environments", Journal of Electrochemical Society, 150 (2), pp. H33-H37, (2003).

P.E. Tsiakaras, et al, "The Oxidation of Ethanol Over Pt Catalyst-Electrodes Deposited on $ZrO_2$ (8 mol% $Y_2O_3$)", Solid State Ionics, 152-153, (2002) pp. 721-726, 2002.

ChunJie Fan, et al, "Studies of Surface Processes of Electrocatalytic Reduction of $CO_2$ on Pt(210), Pt(310) and Pt(510)", Science in China Series B: Chemistry, vol. 50 No. 5, Oct. 2007, pp. 593-598.

Nagahiro Hoshi, et al, "Electrochemical Reduction of Carbon Dioxide on Kinked Stepped Surfaces of Platinum Inside the Stereographic Triangle", Journal of Electroanalytical Chemistry, 540 (2003), pp. 105-110.

Na Tian, et al, "Synthesis of Tetrahexahedral Platinum Nanocrystals with High-Index Facets and High Electro-Oxidation Activity", Science, vol. 316 May 4, 2007, pp. 732-735.

Christos Kokkofitis, et al, "Catalytic Study and Electrochemical Promotion of Propane Oxidation on Pt/YSZ", Journal of Catalysis, 234 (2005), pp. 476-487.

P. Vernoux, et al, "Electrochemical Promotion of Propane and Propene Oxidation on Pt/YSZ", Journal of Catalysis, 208, (2002) pp. 412-421.

Aman Arora, "Ceramics in Nanotech Revolution", Advanced Engineering Materials, vol. 6 No. 4 (2004), pp. 244-247.

"Interdisciplinary Research Center for Catalysis", Technical University of Denmark, Annual Report 2001, pp. 1-34.

Worapon Kiatkittipong, et al, "TPD Study in LSM/YSZ/LaAlO System for the Use of Fuel Cell Type Reaction", Solid State Ionics, 166 (2004), pp. 127-136.

Thème IES "Promotion Électrochimique de Réactions Catalytiques (effet NEMCA)" (undated).

"Advanced Propulsion Systems and Emission Reduction Technologies—PREMTECH", Thematic Network, Final Report, pp. 1-34, (2007).

D. Tsiplakides, et al, "Work Function and Catalytic Activity Measurements of an $IrO_2$ Film Deposited on YSZ Subjected to In Situ Electrochemical Promotion", J. Electrochem. Soc., vol. 145 No. 3, Mar. 1998, pp. 905-908.

E.A. Baranova, et al, "Electrochemical Promotion of Ethylene Oxidation over Rh Catalyst Thin Films Sputtered on YSZ and $TiO_2$/YSZ Supports", Journal of Electrochemical Society, 152 (2), pp. E40-E49, (2005).

Ilan Riess, et al, "Fermi Level and Potential Distribution in Solid Electrolyte Cells With and Without Ion Spillover", Solid State Ionics, 159 (2003), pp. 313-329.

P. Vernoux, et al, "Coupling Catalysis to Electrochemistry: A Solution to Selective Reduction of Nitrogen Oxides in Lean-Burn Engine Exhausts?" Journal of Catalysis, vol. 217 (2003), pp. 203-208.

Bijan Miremadi, et al, "Low-Temperature Hydrogen Production Using Electrically Activated Catalysts", Chem. Commun., 2000, pp. 1875-1876.

Ezequiel P.M. Leiva, et al, "NEMCA Effect: Why Are the Work Function Changes of the Gas Exposed Catalyst-Electrode Surface One-to-One Related to the Changes in the Catalyst Working Electrode Potential?", Journal of Solid State Electrochemistry (2003), pp. 1-13.

S.G. Neophytides, et al, "Selective Interactive Grafting of Composite Bifunctional Electrocatalysts for Simultaneous Anodic Hydrogen and CO Oxidation", Journal of Electrochemical Society, 150 (10), (2003) pp. E512-E526.

C. N. Costa, et al., "Mathematical Modeling of the Oxygen Storage Capacity Phenomenon Studied by CO Pulse Transient Experiments Over $Pd/CeO_2$ Catalyst," Journal of Catalysis 219 (2003) pp. 259-272.

Alfred B. Anderson, et al. "Mechanism for the Electro-oxidation of Carbon Monoxide on Platinum, Including Electrode Potential Dependence," Journal of the Electrochemical Society, 149 (10) (2002) pp. E383-E388.

Jingxin Zhang, et al., "Mechanistic and Bifurcation Analysis of Anode Potential Oscillations in PEMFCs with CO in Anode Feed", Journal of the Electrochemical Society, 151 (5) (2004) pp. A689-A697.

C. Pliangos, et al. "Electrochemical Promotion of the Reduction of NO in Presence of Oxygen." University of Patras, Department of Chemical Engineering, Greece, One page (undated).

Raymond J. Gorte, et al. "Novel SOFC Anodes for the Direct Electrochemical Oxidation of Hydrocarbons," University of Pennsylvania, Department of Chemical and Biomolecular Engineering, 20 pages, (2003).

B.S. Bal'zhinimaev, et al. "Phase Transition in a Bed of Vanadium Catalyst for Sulfuric Acid Production: Experiment and Modeling," Chemical Engineering Journal 84 (2001) pp. 31-41.*

D. Hamilton, Methods of Conserving Archaeological Material from Underwater Sites, Jan. 1, 1999, Rev. 1, Anthropology 605, Conservation of Archaeological Resources 1, pp. 79-83.

* cited by examiner

NMR analysis of the reaction product at 900 C.

NMR analysis of the reaction product at 600 C.

Pt EIS

METHODS AND APPARATUS FOR THE SYNTHESIS OF USEFUL COMPOUNDS

This application claims the benefit of U.S. provisional patent application no. 60/994,854 filed on Sep. 20, 2007, which is incorporated herein and made a part hereof by reference for all purposes as if set forth in its entirety.

BACKGROUND OF THE INVENTION

The present invention relates to methods and apparatus for the activation of a low reactivity, non-polar chemical compound. More specifically, the present invention relates to process for the synthesis of useful compounds from non-polar compounds such as carbon dioxide and the like.

The chemical reduction of carbon dioxide using molecular hydrogen is not thermodynamically viable. However, the possibility to use activated hydrogen-containing compounds for the preparation of useful products from carbon dioxide is intriguing.

Some catalysts, e.g., transition metal complexes, have been shown to catalyze the reduction of carbon dioxide via hydride complexes, in which the origin of the activated hydrogen is water. Such reactions result usually in a partial reduction of carbon dioxide to carbon monoxide. However, the possibility of the further reduction to formaldehyde, methanol and/or methane is potentially very significant. Such reduction products are particularly important in chemical manufacture (formaldehyde and methanol), as well as fuels (methanol and methane). [see, e.g., "Thermodynamic, Kinetic and Product Considerations in Carbon Dioxide Reactivity", F. R. Keene, Chapter 1 in monograph "Electrochemical and Electrocatalytic Reactions of Carbon Dioxide" (B. P. Sullivan, K. Krist, and H. E. Guard, eds.); Elsevier (Amsterdam), 1993].

In particular, formaldehyde and its derivatives serve a wide variety of end uses such as for plastics and coatings. Formaldehyde is considered one of the world's most important industrial and research chemicals, owing to the vast number of chemical reactions it can participate in.

As formaldehyde polymerizes readily in the presence of minute amounts of impurities, the commercial forms usually available comprise:

the polymer form, which can be reversibly converted to a monomer by the reaction of heat or an acid:

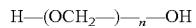

the cyclic trimeric form, called trioxane; and the aqueous solution in which over 99 of formaldehyde is present as hydrate or a mixture of oxymethylene glycol oligomers.

It would be advantageous to provide methods and apparatus for activation of a low reactivity, non-polar chemical compound. In particular, it would be advantageous to provide methods and apparatus for the reduction of carbon dioxide without the need to use molecular hydrogen. It would be further advantageous to enable the reduction of carbon dioxide using water or steam as the source of hydrogen. It would also be advantageous to enable the oxidation or reduction of benzene to derivative compounds, such as acetophenone, a phenol, cyclohexane, or other benzene derivatives. Another advantageous possibility is to provide the capability of achieving a further reduction of formaldehyde-derived polymers to higher molecular mass alcohols and to olefins.

The methods and apparatus of the present invention provide the foregoing and other advantages.

SUMMARY OF THE INVENTION

The present invention relates to methods and apparatus for activation of a low reactivity, non-polar chemical compound. In one example embodiment, the method comprises introducing the low reactivity chemical compound to a catalyst. At least one of (a) an oxidizing agent or a reducing agent, and (b) a polar compound is provided to the catalyst and the chemical compound. An alternating current is applied to the catalyst to produce an activation reaction in the chemical compound. This activation reaction produces a useful product.

The activation reaction may comprise one of a reduction or an oxidation reaction. The polar compound may comprise one of water or steam. One of ammonia, nitric oxide, carbon monoxide, methane, or the like may be added to the water or steam.

In another example embodiment, the polar compound may comprise one of water, ammonia, nitric oxide, and carbon monoxide. Those skilled in the art will appreciate that other polar compounds may be used with the present invention.

In a further example embodiment, the chemical compound and the at least one of the oxidizing agent or the reducing agent and the polar compound may be introduced into a chamber containing the catalyst.

In one example embodiment, the low reactivity chemical compound may comprise $CO_2$. In such an embodiment, the useful product may comprise formaldehyde in at least one of a monomeric and a polymeric form. In other example embodiments, the useful product may comprise at least one of an aldehyde, trioxane, ethane, ethylene, formaldehyde, and paraformaldehyde. The useful products may contain at least one of carbon, hydrogen, and oxygen. Still further, the useful products may comprise at least one of an alcohol compound and an olefin.

In a further example embodiment, the chemical compound may comprise an aromatic compound. The aromatic compound may comprise benzene or a benzene derivative. In such an embodiment, a reducing agent such as hydrogen may be provided to the catalyst and the aromatic compound, and the useful product may comprise cyclohexane or a benzene derivative. Alternatively, an oxidizing agent such as oxygen may be provided to the catalyst and the aromatic compound, and the useful product may comprise at least one of acetophenone, a phenol, or a benzene derivative.

The catalyst may comprise one of a precious metal, a semi-conducting oxide, a semi-conducting cermet, and a varistor. Examples of catalysts that may be used with the present invention include, but are not limited to catalysts comprising platinum, platinum black, rhodium, rhodium black, palladium, palladium black, silver, manganese oxide, a manganese oxide derivative, molybdenum oxide, a molybdenum oxide derivative, iron oxide, an iron oxide derivative, cerium oxide, a cerium oxide derivative, titanium oxide, doped titanium oxide and related compounds, cobalt oxide, rhodium oxide, zinc oxide, and the like.

In one example embodiment, the catalyst may comprise a catalyst layer applied to a porous ceramic substrate. The catalyst layer may be supported by a layer of a solid electrolyte. The solid electrolyte layer may be one of a continuous layer or a discontinuous layer. The solid electrolyte may comprise one of stabilized zirconia (stabilized with, e.g., gadolinium oxide, samarium oxide, lanthanum oxide, ytterbium oxide, yttrium oxide or other adequate materials known to those skilled in the art), Nafion, other hydrogen ion conducting materials, beta aluminas, or the like The alternating current may be applied across a three-phase boundary at an interface between the catalyst and the solid electrolyte layer. In order to apply the alternating current to the catalyst layer, three electrodes may be provided. For example, a reference electrode may be applied to the solid electrolyte layer, a counter electrode may be applied between the catalyst and the solid electrolyte layer, and a working electrode may be applied to the catalyst layer.

In a further example embodiment, a polarization impedance of the supported catalyst layer may be monitored. The polarization impedance may be controlled by varying the alternating current, enabling optimization of the activation reaction.

In addition, a controlled oxygen partial pressure environment may be provided at a level of the supported catalyst layer. The partial pressure of the oxygen at a level of the catalyst layer may be monitored. The monitoring of the partial pressure of the oxygen may comprise monitoring an interfacial impedance of the supported catalyst layer. The partial pressure of oxygen at a level of the catalyst layer may then be determined as a function of the interfacial impedance. Alternately, the polarization impedance of the supported catalyst layer may be monitored, and the partial pressure of oxygen at the level of the catalyst layer may be determined as a function of the monitored polarization impedance.

In addition, a momentary value of the alternating current may be determined as a function of the monitored polarization impedance.

The amount of the at least one of the oxidizing agent, the reducing agent, and the polar compound provided may be controlled in order to optimize the activation reaction. Further, a ratio of an amount of the chemical compound to an amount of the at least one of the oxidizing agent, the reducing agent, and the polar compound provided may be controlled in order to optimize the activation reaction.

In a further example embodiment, heat may be applied to the catalyst in order to optimize the activation reaction.

The present invention also generally includes a method for activation of a chemical compound. The chemical compound is introduced to a catalyst. An oxidizing agent or a reducing agent is provided to the catalyst and the chemical compound. An alternating current is applied to the catalyst to produce an activation reaction in the chemical compound. This activation reaction produces a useful product. For example, the chemical compound may comprise a polar compound and the oxidizing or reducing agent may comprise a polar reactant or a nonpolar reactant. Additionally, the chemical compound may comprise a nonpolar chemical compound and the oxidizing or reducing agent may comprise a polar reactant or a nonpolar reactant.

The present invention also encompasses apparatus for activation of a low reactivity, non-polar chemical compound which can be used to carry out the various embodiments of the methods discussed above. The apparatus may comprise a catalyst, a means for introducing the low reactivity chemical compound to the catalyst, a means for providing at least one of (a) an oxidizing agent or a reducing agent, and (b) a polar compound to the catalyst and the chemical compound, and means for applying an alternating current to the catalyst to produce an activation reaction in the chemical compound, such that the activation reaction produces a useful product.

BRIEF DESCRIPTION OF THE DRAWINGS

The present invention will hereinafter be described in conjunction with the appended drawing figures, wherein like reference numerals denote like elements, and.

DETAILED DESCRIPTION

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The present invention is the product of a joint research agreement between Catelectric Corp. (Catelectric) and The University of Connecticut and relates to methods and apparatus for activation of a low reactivity, non-polar chemical compound in order to produce useful products. In particular, the present invention relates to methods and apparatus for the preparation of useful products, such as, e.g., paraformaldehyde, via the activation (e.g., reduction or oxidation) of carbon dioxide, using water as the source of hydrogen and oxygen. However, as will be explained in detail below, the present invention is not limited to such reactions and products. The reaction is activated via the DECAN™ process developed by Catelectric. The DECAN™ process is described in Catelectric's U.S. Pat. No. 7,325,392 issued on Feb. 5, 2008 and entitled "Control Systems for Catalytic Processes" and in Catelectric's pending in U.S. patent application Ser. No. 11/588,113 filed on Oct. 25, 2006 entitled "Methods and Apparatus for Controlling Catalytic Processes, Including Catalyst Regeneration and Soot Elimination" (published as 2007/0095673), both of which are incorporated herein and made a part hereof by reference.

Figure 1:
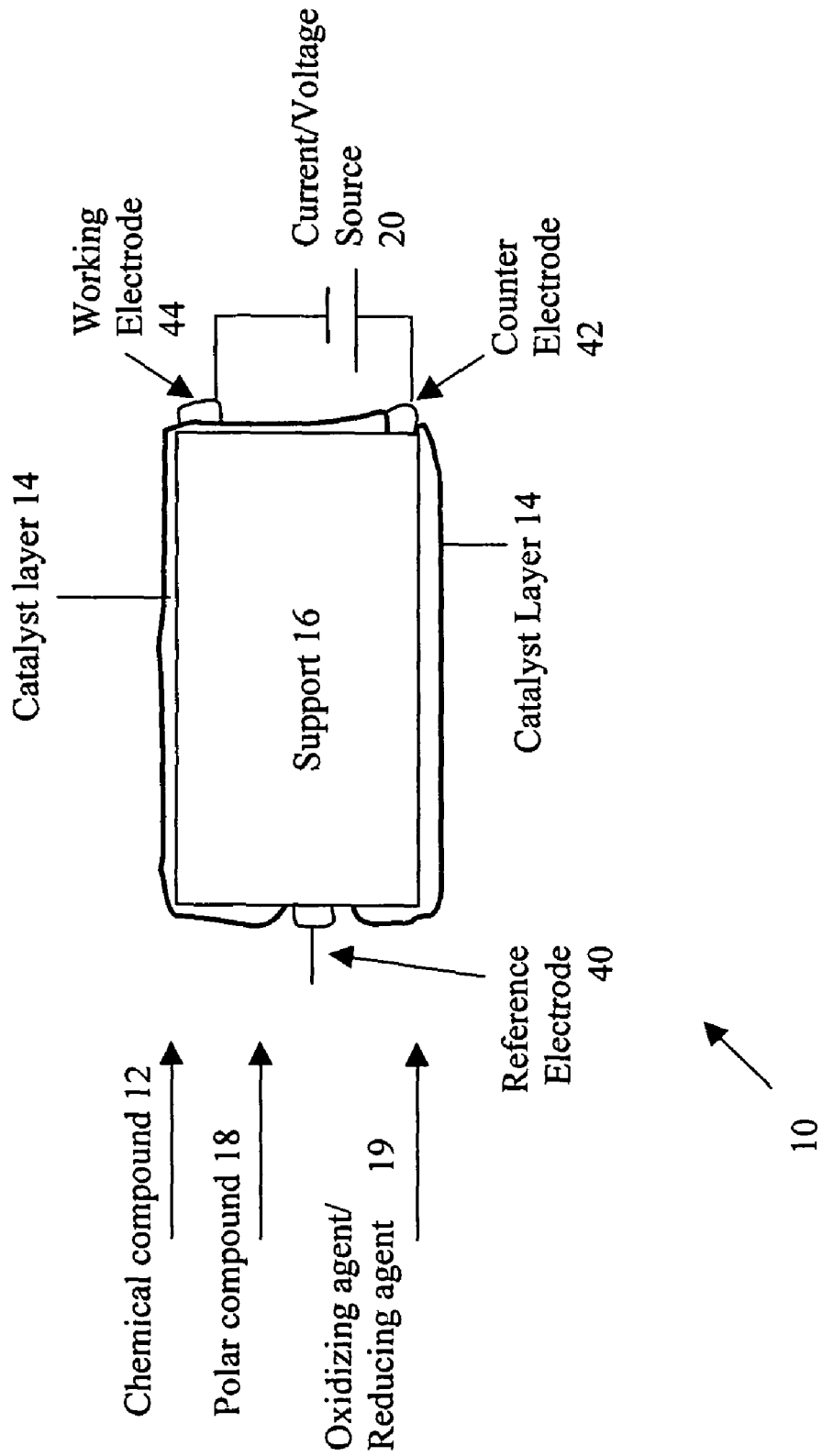
FIG. 1 shows an example embodiment of an apparatus in accordance with the present invention.

The present invention relates to methods and apparatus for activation of a low reactivity, non-polar chemical compound. FIG. 1 shows an example embodiment of an apparatus 10 for activation of a low reactivity, non-polar chemical compound. A low reactivity chemical compound 12 is introduced to a catalyst (e.g., catalyst layer 14). The catalyst layer 14 may be supported on a support 16. At least one of (a) an oxidizing agent or a reducing agent 19, and (b) a polar compound 18 is provided to the catalyst 14 and the chemical compound 12. An alternating current (e.g., from current/voltage source 20) is applied to the catalyst 14 to produce an activation reaction in the chemical compound 12. This activation reaction produces a useful product.

It should be appreciated that the term "non-polar chemical compound" as used herein denotes a chemical compound which, as a whole, has a zero permanent dipole moment. For example, by this definition, $CO_2$ is considered to be non-polar, even though it has polar bonds between the individual molecules. Accordingly, the term "polar compound" as used herein denotes a compound that, as a whole, has a non-zero dipole moment.

The activation reaction may comprise one of a reduction or an oxidation reaction. The polar compound 18 may comprise one of water or steam. One of ammonia, nitric oxide, carbon monoxide, methane, or the like may be added to the water or steam.

In another example embodiment, the polar compound 18 may comprise one of water, ammonia, nitric oxide, and carbon monoxide. Those skilled in the art will appreciate that other polar compounds may be used with the present invention. Further, those skilled in the art will appreciate that the use of water (or steam) will facilitate both an oxidation and a reduction reaction.

Figure 2:
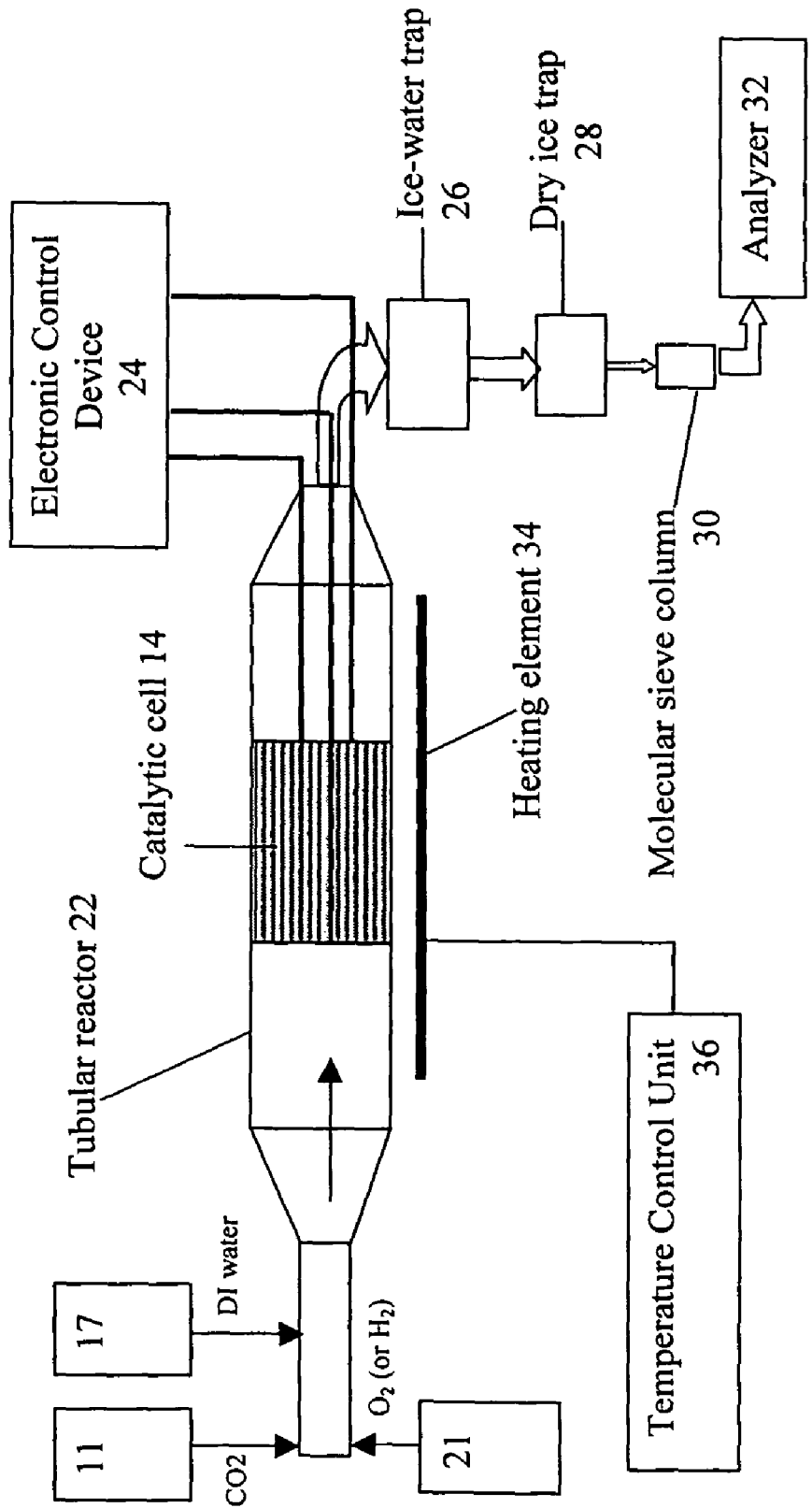
FIG. 2 shows a further example embodiment of an apparatus in accordance with the present invention.

In a further example embodiment as shown in FIG. 2, the chemical compound 12 and the at least one of the oxidizing agent or the reducing agent 19 and the polar compound 18 may be introduced into a chamber 22 containing the catalyst 14. The chamber 22 may comprise a tubular reactor. The alternating current may be controlled by an electronic control device 24. The chemical compound 12 (e.g., $CO_2$) may be introduced to the chamber 22 from a gas tank 11. The polar compound 18 (e.g., water) may be introduced to the chamber 22 from a peristaltic pump 17. The oxidizing agent (e.g., oxygen) or the reducing agent (e.g. hydrogen) 19 may be introduced from tank 21. After passing the chemical compound 12 and at least one of the oxidizing agent or the reducing agent 19 and the polar compound 18 through the chamber 22 containing the catalyst 14 and applying the alternating current thereto, the resulting products of the reaction may be passed through an ice-water trap 26 and/or a dry ice/liquid nitrogen trap 28 before being separated in a molecular sieve 30 prior to computer analysis (such as gas chromatography-mass spectrometry (GC-MS), high performance liquid chromatography-mass spectrometry (HPLC-MS), nuclear magnetic resonance (NMR) and other analysis techniques) at analyzer 32.

In one example embodiment, the low reactivity chemical compound 12 may comprise $CO_2$. In such an embodiment, the useful product may comprise formaldehyde in at least one of a monomeric and a polymeric form. In other example embodiments, the useful product may comprise at least one of an aldehyde, trioxane, ethane, ethylene, formaldehyde, and paraformaldehyde. The useful products may contain at least one of carbon, hydrogen, and oxygen. Still further, the useful products may comprise at least one of an alcohol compound and an olefin. Also, oxygen ($O_2$) may be a result of the reaction.

In a further example embodiment, the chemical compound 12 may comprise an aromatic compound. The aromatic compound may comprise benzene or a benzene derivative. In such an embodiment, the reducing agent 19 (such as hydrogen) may be provided to the catalyst and the aromatic compound, and the useful product may comprise cyclohexane or a benzene derivative. Alternatively, an oxidizing agent 19 (such as oxygen) may be provided to the catalyst and the aromatic compound, and the useful product may comprise at least one of acetophenone, a phenol, or a benzene derivative.

The catalyst 14 may comprise one of a precious metal, a semi-conducting oxide, a semi-conducting cermet, and a varistor. Examples of catalysts that may be used with the present invention include, but are not limited to catalysts comprising platinum, platinum black, rhodium, rhodium black, palladium, palladium black, silver, manganese oxide, a manganese oxide derivative, molybdenum oxide, a molybdenum oxide derivative, iron oxide, an iron oxide derivative, cerium oxide, a cerium oxide derivative, titanium oxide, doped titanium oxide and related compounds, cobalt oxide, rhodium oxide, zinc oxide, and the like. Further examples for catalyst material may generally include oxides of alkali metals, alkaline earths, lanthanides, actinides, transition metals, and nonmetals.

Figure 3:
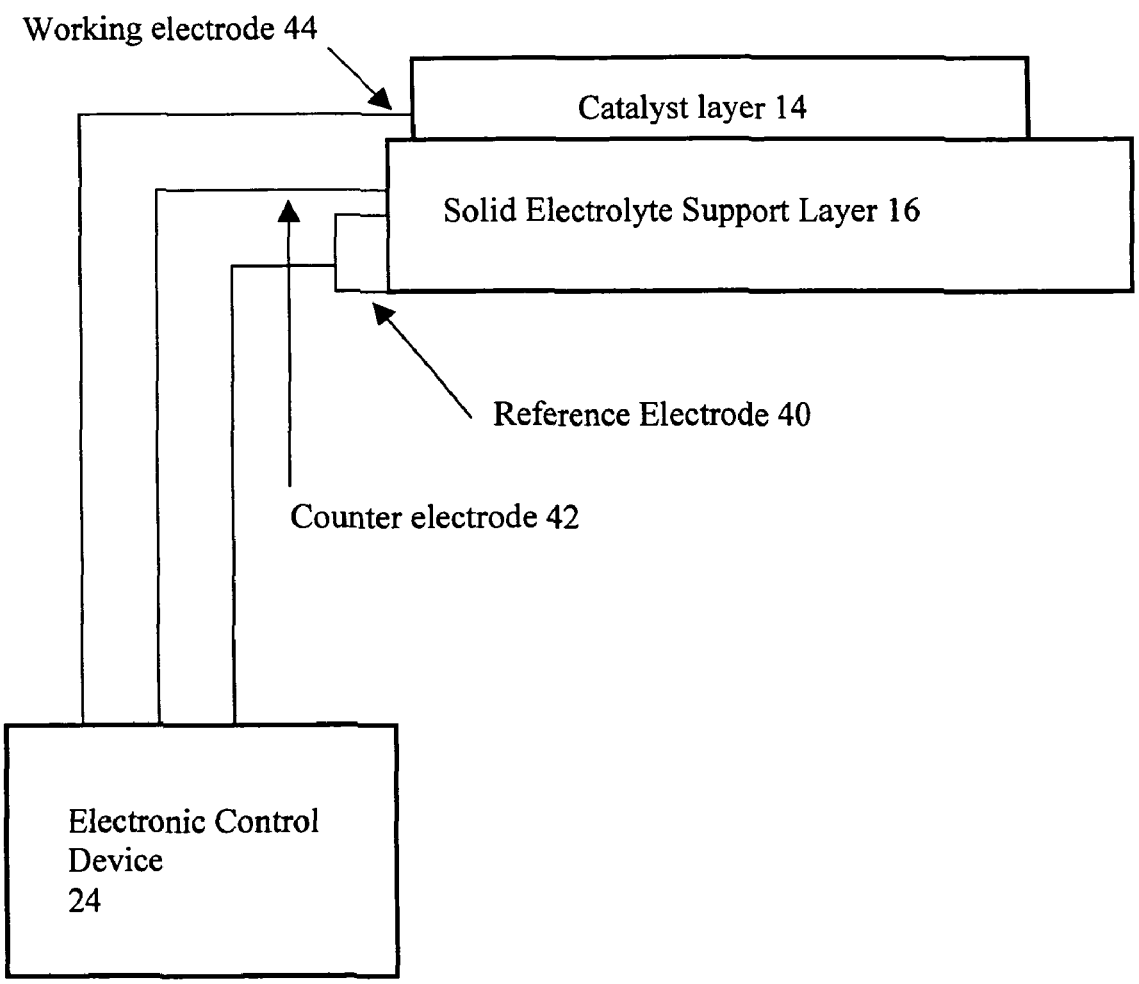
FIG. 3 shows an example embodiment of an electrode arrangement in accordance with the present invention.

In one example embodiment as shown in FIG. 3, the catalyst 14 may comprise a catalyst layer applied to a support 16 such as porous ceramic substrate. For example, the catalyst layer 14 may be supported by a layer 16 of a solid electrolyte. In certain embodiments, the catalyst 14 may be applied to the solid electrolyte layer 16, which in turn may be applied onto a separate support (not shown). The solid electrolyte layer 16 may be one of a continuous layer or a discontinuous layer. The solid electrolyte 16 may comprise one of stabilized zirconia (stabilized with, e.g., gadolinium oxide, samarium oxide, lanthanum oxide, ytterbium oxide, yttrium oxide or other adequate materials known to those skilled in the art), Nafion, other hydrogen ion conducting materials, beta aluminas, or the like. The temperature range of the reactor will be determined by the specific properties of these materials, known to those skilled in the art.

The alternating current may be applied across a three-phase boundary at an interface between the catalyst 14 and the solid electrolyte layer 16 via the electronic control device 24. In order to apply the alternating current to the catalyst layer 14, three electrodes may be provided. For example, a reference electrode 40 may be applied to the solid electrolyte layer 16, a counter electrode 42 may be applied to the solid electrolyte layer 16, and a working electrode 44 may be applied to the catalyst layer 14.

In a further example embodiment, a polarization impedance of the supported catalyst layer 14 may be monitored. In order to monitor the polarization impedance, the electronic control device 24 may include means for determining the applied current and voltage. The determination of the polarization impedance from the sensed current is explained in detail in Catelectric's U.S. Pat. No. 7,325,392. The polarization impedance may be controlled by varying the alternating current from electronic control device 24, enabling optimization of the activation reaction.

In addition, a controlled oxygen partial pressure environment may be provided at a level of the supported catalyst layer. The oxygen may be produced from the solid electrolyte layer 16 under the voltage applied between the working electrode 44 and the reference electrode 40, and is a function of the DECANT process. Alternately, the oxygen may be provided from tank 21 (FIG. 2). The partial pressure of the oxygen at a level of the catalyst layer 14 may be monitored. The determining of the partial pressure of oxygen may also be achieved via the electronic control device 24 as a function of a voltage measurement. For example, a monitoring of the partial pressure of the oxygen may comprise monitoring an interfacial impedance of the supported catalyst layer 14. The partial pressure of oxygen at a level of the catalyst layer 14 may then be determined as a function of the interfacial impedance. Alternately, the polarization impedance of the supported catalyst layer 14 may be monitored as discussed above, and the partial pressure of oxygen at the level of the catalyst layer 14 may be determined as a function of the monitored polarization impedance (e.g., achieved via the electronic control device 24).

In addition, a momentary value of the alternating current may be determined by the electronic control device 24 as a function of the monitored polarization impedance.

The amount of the oxidizing agent or the reducing agent 19 and/or the polar compound 18 provided may be controlled in order to optimize the activation reaction. Further, a ratio of an amount of the chemical compound 12 to an amount of the oxidizing agent or the reducing agent 19 and/or the polar compound 18 provided may be controlled in order to optimize the activation reaction.

In a further example embodiment, heat may be applied to the catalyst in order to optimize the activation reaction. Heat may be applied via heating element 34, which is controlled by temperature control unit 36 (FIG. 2). Oxygen 19 may be applied from an oxygen source (e.g., tank 21) or may be generated by controlling the voltage applied to the solid electrolyte layer, as discussed above.

The present invention also generally includes a method for the activation of a chemical compound. The chemical compound 12 is introduced to a catalyst 14. An oxidizing agent or a reducing agent 19 is provided to the catalyst 14 and the chemical compound 12. An alternating current is applied to the catalyst 14 to produce an activation reaction in the chemical compound 12. This activation reaction produces a useful product. For example, the chemical compound may comprise a polar compound 12 and the oxidizing or reducing agent 19 may comprise a polar reactant (e.g., water or steam) or a non-polar reactant (oxygen or hydrogen). Additionally, the chemical compound may comprise a non-polar chemical compound 12 (as discussed above) and the oxidizing or reducing agent 19 may comprise a polar reactant (e.g., water or steam) or a non-polar reactant (oxygen or hydrogen). For example, one polar compound like methanol could react with another polar compound like ethanol to form products of value, or one non-polar compound like benzene could react with another nonpolar compound like methane to form products of value.

The examples below illustrate example embodiments of a process for the reduction of carbon dioxide using water as the source of hydrogen in accordance with the present invention. The examples below were carried out using the apparatus described above in connection with FIG. 2. However, it should be appreciated by those skilled in the art that the inventive process is not limited by the following examples and may be implemented for the reduction of other molecules, e.g., higher molecular mass alcohols to olefins and other compounds.

EXAMPLE 1 a. Substrates: Commercial Calcia Fully Stabilized Zirconia (FSZ) porous ceramics from Vesuvius Hi-Tech Ceramics was used as the solid electrolyte layer 16.
b. Deposition of the catalyst: Liquid-Phase Chemical Vapor Deposition (LP-CVD) was used for coating of the catalyst layer 14 (platinum). Pt(acac)$_2$ (Strem Chemicals Inc.) was used as the platinum precursor. The temperature of the precursor was set at 120-150 C, while the temperature of the FSZ (calcia) was set at 400-500 C. Argon was used as the carrier gas. The carrier gas flow rate of the precursor was 500-1000 sccm/min, and the carrier gas was heated to 100-150 C before being introduced into the CVD synthesis tube. Oxygen was used as an oxidant. The oxygen flow rate was set at 80-200 sccm/cm. The total pressure of the CVD reactor was controlled at 5-20 KPa. The platinum deposition time was 1-4 hours.
c. Assembling of three electrodes: Three electrodes were deposited on the FSZ (calcia) ceramic catalyst as described above in connection with FIG. 3. The three electrodes each comprise 0.25 mm platinum wires (Alfa Aesar). The three platinum wires were assembled on the FSZ (calcia) using platinum paste (from Engelhard/BASF) and then treated in air at 900° C. The reference electrode 40 was directly connected to the support 16 without contact with the platinum layer 14. The counter electrode 42 was assembled before the deposition of the catalyst layer 14 of LP-CVD of platinum, and is in contact with the FSZ support layer 16. The working electrode 44 was deposited on the platinum LP-CVD catalyst layer 14. After assembling the three electrodes, the catalyst assembly with three electrodes was placed in a quartz tube and reduced in 8% hydrogen/helium mixed gas at 600-800° C. for 4-6 hours.
d. Catalytic reaction—reactor and reaction parameters: The supported Pt-FSZ catalyst assembly, with the three electrodes, was placed in a quartz tube reactor (e.g., tubular reactor 22 of FIG. 2). The reactor was purged of air and was thereafter operated at slightly positive pressure of about 5-14 psig. The tube reactor temperature was set at 600 to 950° C.

It should be noted that the present invention is not limited to the foregoing description. For example, the temperature may be as low as room temperature or higher than 950° C.; the solid electrolyte can be Nafion, and the catalyst can be platinum black. Other materials for use as the solid electrolyte or catalyst will be apparent to those skilled in the art.

Further, the solid electrolyte layer 16 can be deposited on a support comprising an inert ceramic substrate (e.g., cordierite catalyst supports provided by Corning Inc. or St. Gobain Co) via any of the appropriate methods known to those skilled in the art. Similarly, the catalyst 14 can be deposited on the solid electrolyte layer 16 via any of the appropriate methods known to those skilled in the art.

In addition, the implementation of the process does not require a continuity of the solid electrolyte layer 16 or of the catalyst layer 14. What is necessary is a preponderance of grain boundaries where the catalyst 14 is in contact with the solid electrolyte 16 and sufficient open porosity to allow for the access of the reacting phases to the catalytically active interfaces.

Carbon dioxide ($CO_2$) used was zero grade gas from Airgas. Water used was de-ionized water. Water was injected by a peristaltic pump 17, and evaporated by a heated ceramic tube. $CO_2$ was used as the carrier gas provided from tank 11. The molar ratio of $CO_2$ to water was set at 10 to 1 or 5 to 1. The flow of $CO_2$ was monitored by a mass flow meter and was varied between 200 scc/minute and 1600 scc/minute. It should be noted that the water/$CO_2$ ratio can take any values within the interval 1/1000 to 1000/1, and even outside this range.

The system was polarized (via the electronic control device 24 and three electrodes 40, 42, and 44) with a pulsed current at about 1 kHz at average voltages ranging from 0.03 to 0.1 V rms. The current passed averaged between 0.03 and 0.13 mA. This process is described in detail in U.S. patent application Ser. No. 11/588,113 mentioned above.

Eight runs of polarization were applied, each lasting about 15 minutes.

An unexpected result of this process was that a substantial amount of a white powder was formed, which was collected at the cold areas of the reactor 22, as well as in the water trap 26 and liquid nitrogen trap 28. The gas phase was analyzed by gas chromatography (e.g., analyzer 32) with thermal and flame ionization detectors.

Figure 4:
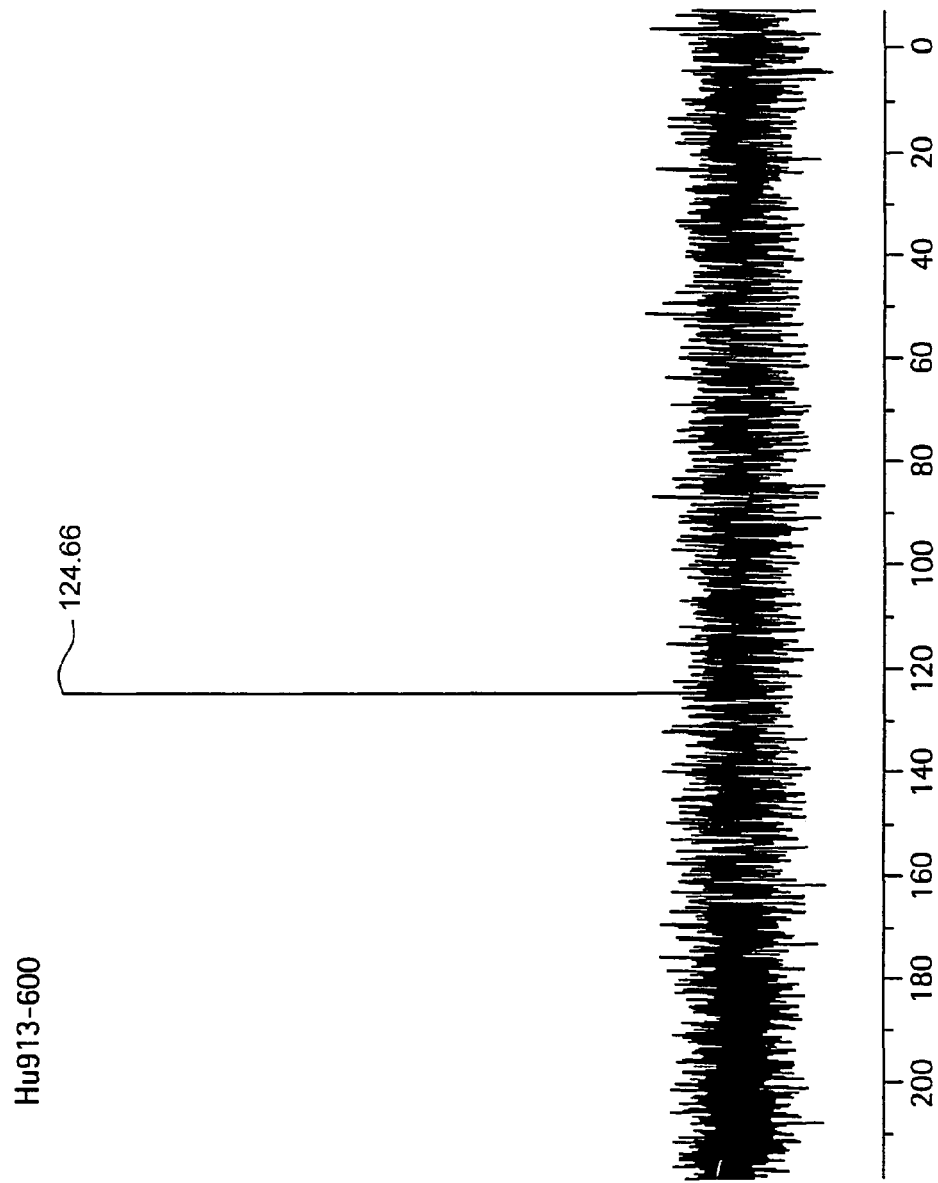
FIG. 4 shows NMR analysis results for the output achieved with one example embodiment of the present invention.

The powder was dispersed in the water samples collected by the traps, which were then analyzed by Nuclear magnetic resonance spectroscopy (NMR) and High-Pressure Liquid Chromatography (HPLC). With the reactor temperature set at 900° C. data collected was consistent with the presence in these samples of paraformaldehyde and small amounts of trioxane. The result of the NMR analysis is shown in FIG. 4.

EXAMPLE 2

Figure 5:
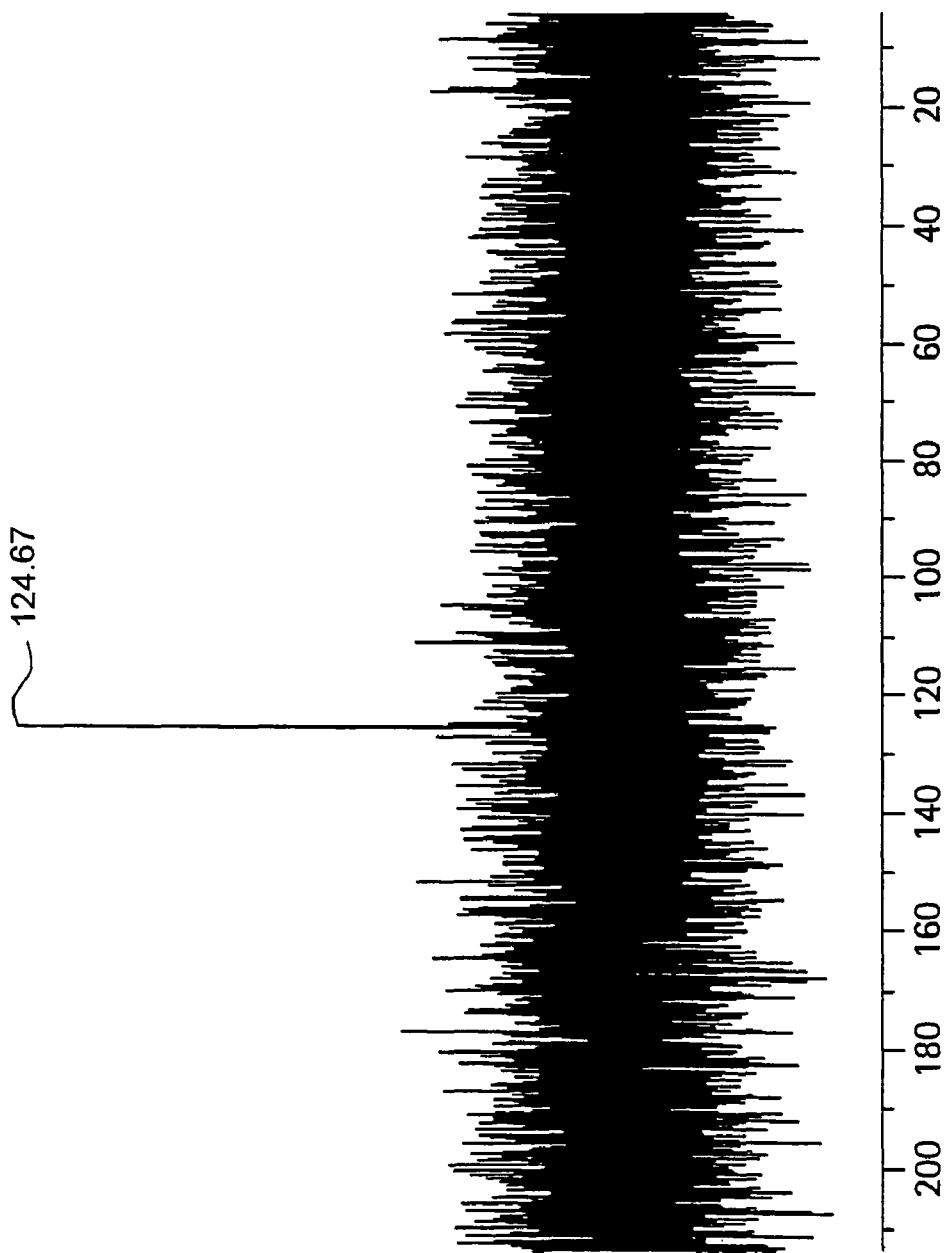
FIG. 5 shows NMR analysis results for the output achieved with a further example embodiment of the present invention.

The catalyst 14 used in this example was the same as that for example 1. The temperature of the quartz tube reactor was set at 600° C. The main product identified by NMR was paraformaldehyde, as shown in FIG. 5.

EXAMPLE 3 a. Substrates: Commercial Calcia Fully Stabilized Zirconia (FSZ) porous ceramics from Vesuvius Hi-Tech Ceramics was used as the solid electrolyte layer 16.
b. Deposition of the catalyst: A catalyst layer 14 of octahedral manganese oxide OMS-2 was prepared as follows: 5.6 g $K_2SO_4$, 8.81 g $K_2S_2O_8$ and 3.77 g $MnSO_4$ and 70 ml DI water were added into a 125 ml autoclave and put into a 4748 Parr acid digestion bomb for 96 hours; the temperature was maintained at 250° C. The solid was washed repeatedly with de-ionized water. The suspension was filtered and stirred overnight at 85° C. into a beaker with 300 ml de-ionized water. The suspension was coated on the Vesuvius porous ceramic body and was dried at 120° C. for 12 hours.
c. Assembly of electrodes: Three platinum electrodes were positioned as described in Example 1. Platinum paste (Engelhard BASF) was applied to assemble the electrodes. Then the catalytic assembly was reduced in 6% Hydrogen/ helium mixed gas for 2 hours at 150-300° C.

The as-prepared catalytic assembly was placed in a tube quartz reactor (tubular reactor 22) and connected with the electronic control device 24. The tube quartz reactor 22 was sealed and isolated with an air environment. $CO_2$ (zero grade from Air gas) was introduced from tank 11 and controlled with a flow meter. Water was injected with a pre-calibrated peristaltic pump 17. Water was heated by a ceramic tube at above 130° C. Then the reactor 22 was purged with $CO_2$.

The system was set at slightly higher atmosphere pressure (for example 5 kpa). The electronic control device 24 supplied polarized current or voltage to the catalytic assembly via electrodes 40, 42, and 44. The tube reactor was set at 250-450° C.

The products were analyzed by NMR and GC techniques.

The Pt-OMS-2 catalyst 14 was tested in the $CO_2$—$H_2O$ system starting from 250° C. and up to 450° C. When the reaction started at 250° C., it was slow. After 4 hours, the sample was analyzed from the first ice water trap 26 by NMR. The resultant NMR patterns did not show any product. The concentration of products may have been out of the limit or the product yield may have been very low. The second test was done at 300° C. The resultant NMR proton patterns showed a low concentration of paraformaldehyde (about 0.5-1.0% in molar). In particular, the NMR results showed a weak peak of paraformaldehyde at this temperature. The third test was done at 400° C. The resultant NMR patterns from the ice water trap 26 and the NMR patterns of the dry ice trap 28 showed stronger peaks of paraformaldehyde at this temperature. The concentration of paraformaldehyde was about 1.0-1.5% in molar. The fourth test was done at 450° C. The resultant NMR proton patterns showed higher concentrations of paraformaldehyde at this temperature. The concentration of paraformaldehyde was about 3.0-5.0% in molar.

For the above four tests, the $CO_2$ flow rate used was 200 sccm, and the water injection rate was 9.16 ml/min. The flow rate of $CO_2/H_2O$ was 2.37.

Based on the above results, the $CO_2$ conversion rate at different temperatures is shown in Table 1 below.

TABLE 1

Conversion rate of carbon dioxide in the reactions at different temperatures

| Temperature(° C.) | Conversion Rate (%) |
|---|---|
| 250 | Low |
| 300 | 0.5-1.0% |
| 400 | 1.0-1.5% |
| 450 | 3.0-5.0% |

EXAMPLE 4

Synthesis of ZnO Catalyst: A low-pressure chemical vapor deposition (LPCVD) technique was used to deposit a catalyst layer 14 of ZnO on a calcium fully stabilized zirconia (FSZ) support 16. The Zn precursor was $Zn(CHCOO)_2$(98+%, Aldrich). The temperature of the FSZ template was set at 300° C. The temperature of precursor was set at 160° C. The deposition pressure was controlled at 3 kPa. The sample was coated two times. In the second run, the position of the sample was reversed (front to back and top bottom of reactor) to get better uniformity of coating. Each coating time was 4 hours. The total CVD coating time was 8 hours. After LPCVD, the sample was heated with a ramp rate at 5° C./min and calcined at 600° C. for 12 hours in air.

Reactor and Electrodes: Three electrodes were assembled on the ZnO-coated FSZ support as described above in connection with FIG. 3. After the ZnO coated FSZ catalyst assembly was calcined, an area of 25 $mm^2$ at the end was pretreated with 5M HCL to remove ZnO. A Platinum reference electrode 40 was assembled at this area. At another end of the cylinder sample, the same method as above was used to remove the ZnO layer, and a platinum wire was connected with the FSZ support layer 16 directly as the counter electrode 42. The working electrode 44 was attached to the ZnO catalyst layer 14. Platinum paste (6082 from BASF) was applied to enable the platinum electrodes to have good contact with the catalyst assembly.

After the electrodes were assembled, the resistance between the electrodes was measured with a Digital Multimeter (HDM350). The results are shown in Table 2 below.

TABLE 2

Resistance between electrodes at different temperatures

| Temp. | Resistance between working electrode and reference electrode | Resistance between working electrode and counter electrode | Resistance between counter electrode and reference electrode |
|---|---|---|---|
| 200° C. | 20M | 135K | >20M |
| 500° C. | 10.5M | 19.6K | 10.1M |
| 600° C. | 1.06M | 5.85K | 0.55M |

The $CO_2$ flow from tank 11 was measured with a flowmeter (OMEGA FL-3504G). Water injection was measured by a calibrated peristaltic pump 17 (Watson Marlow Sci400). Water was dropped on heated ceramic frit (>130° C.) and evaporated in a T tube. Then water was introduced into the reactor with the $CO_2$ carrier gas. ZnO-FSZ catalyst assembly was placed into a 2-inch quartz tube reactor (e.g., tubular reactor 22). The reactor 22 was heated to 600-700° C. with a tube furnace (Thermolyne 21100) or via heating element 34. The ZnO-FSZ catalyst assembly was connected with the three electrodes to the electronic control device 24 and polarized by a voltage or a current controlled by the electronic control device 24. The outflow products were cooled by an ice-water trap 26 and a dry ice trap 28. The gas from the reactor was dried by a molecular sieve column 30, then the gas composition was analyzed with an analyzer 32 (e.g., a gas chromatograph (SRI 8610C)).

A voltage of −2.5V to 2.5V was applied for the polarization tests for with a potentiostatic EIS mode or single frequency mode. The temperature of $CO_2$ and $H_2O$ was set at 600 and 700° C. The flow rate of $CO_2$ was between 200-500 sccm. The ratio of $CO_2/H_2O$ was set at 1:1 and 1:3 respectively. With different polarization, each EIS spectrum was taken by a Gamry Reference 600.

Figure 6:
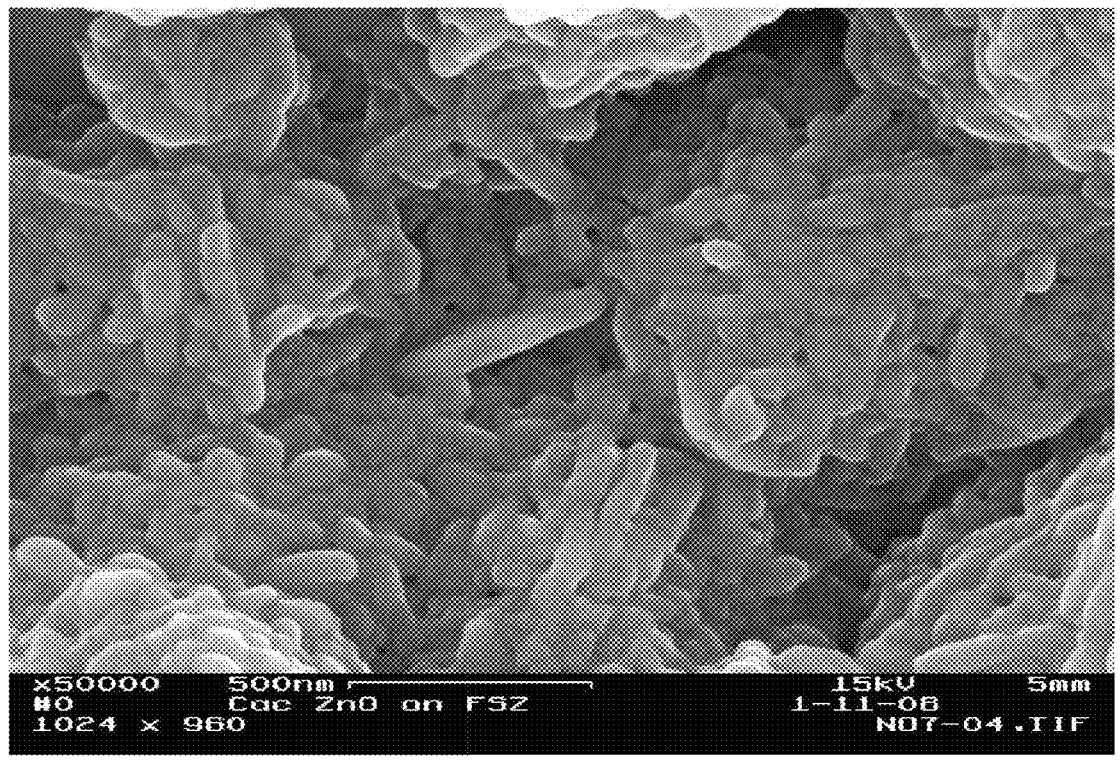
FIGS. 6 and 7 show scanning electron microscopy images of the catalyst assembly at different resolutions, respectively, in accordance with an example embodiment of the invention.
Figure 7:
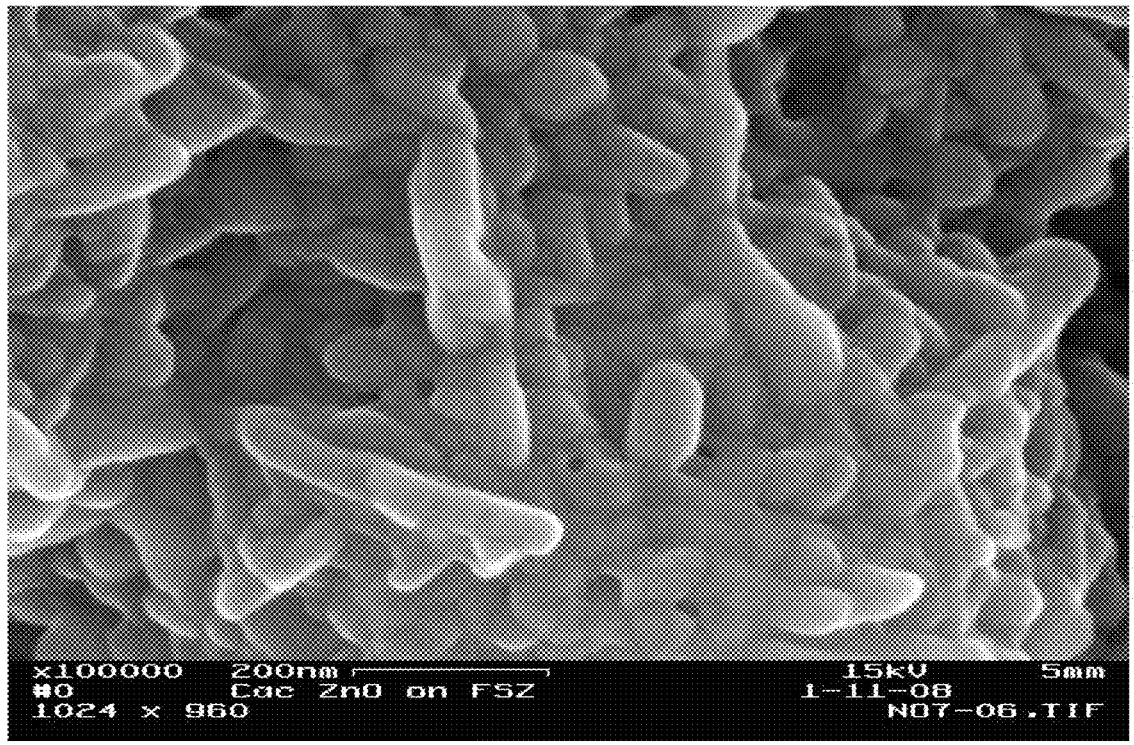

The ZnO coated FSZ assembly was investigated by scanning electron microscopy (SEM). The morphology of the ZnO catalyst layer 14 is shown in FIG. 6 (×50000) and FIG. 7 (×100000). Based on SEM images, the morphologies suggest that the ZnO catalyst layer 14 is continuous and the ZnO particle size is about 20-50 nm.

Figure 8:
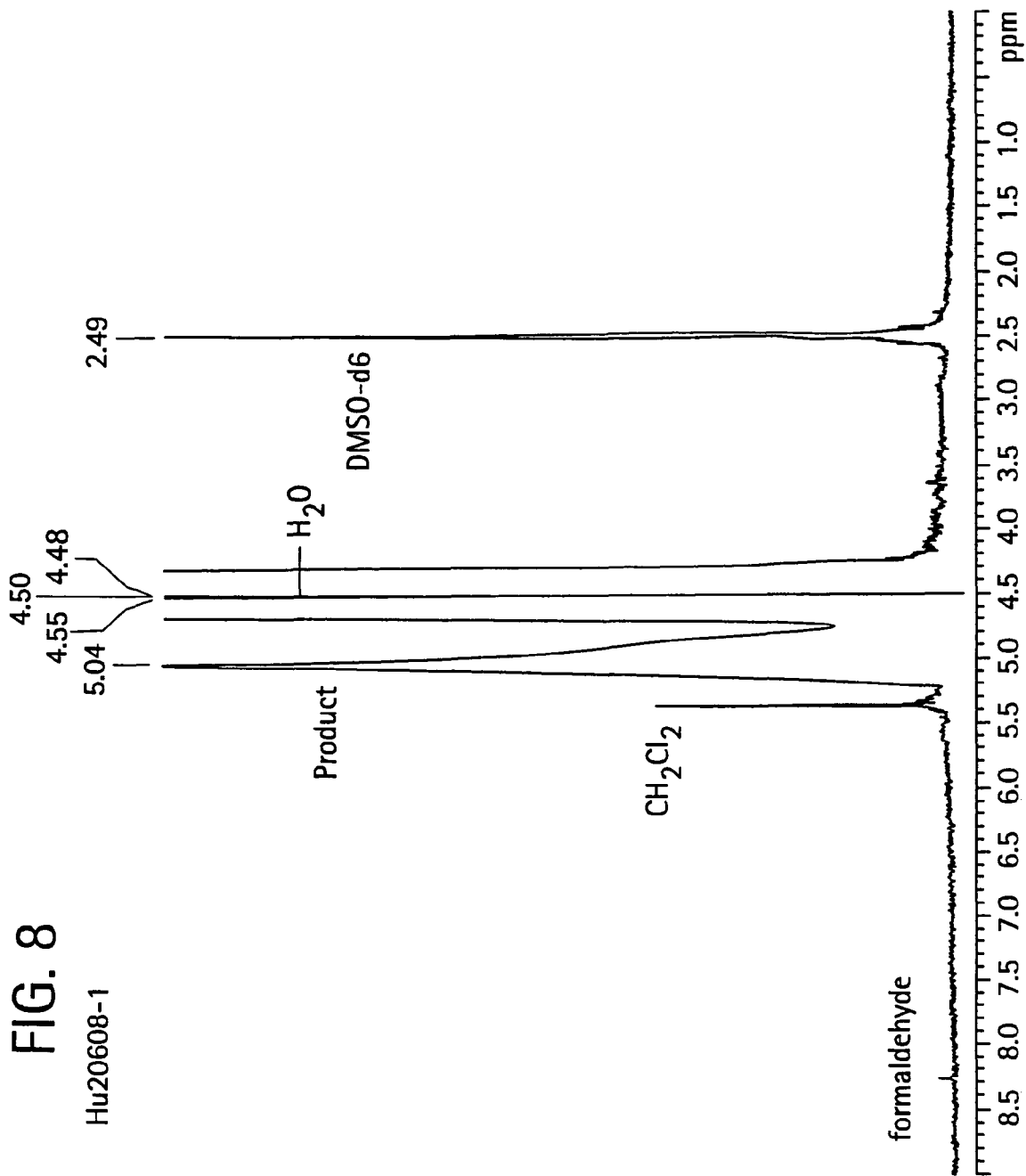
FIG. 8 shows an NMR spectrum for the output achieved with a further example embodiment of the present invention.

The products of $CO_2$ and $H_2O$ activation were separated into two phases: liquid phase and gas phase. Liquid phase products were characterized by NMR and gas phases were analyzed with an SRI 8610C gas chromatograph. Other techniques such as HPLC-MS and GC-MS may also be employed. FIG. 8 is a proton NMR spectrum of the synthesized products. The $CO_2$ flow rate was set at 320-450 sccm; water was injected with a flow rate of 10 mL/hour (or 207 sccm/min). The $CO_2/H_2O$ molar ratio was 1.6-2.2. Based on the results shown in FIG. 8, one major product was synthesized. The NMR chemical shift is between 4.75 to 5.20 ppm. Small amounts of formaldehyde were present at a chemical shift of 8.25 ppm.

Figure 9:
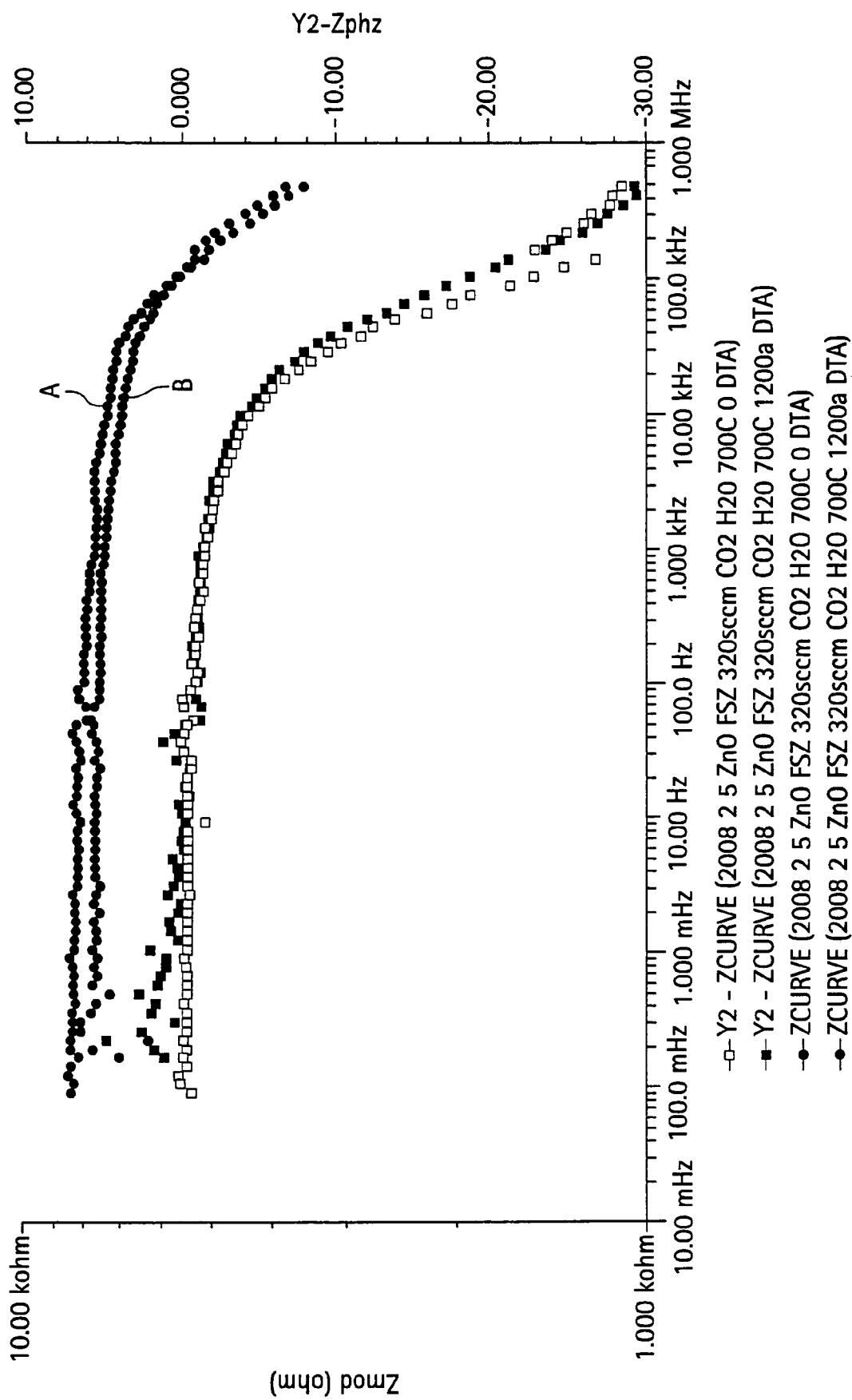
FIG. 9 shows a polarization Bode spectrum from one example embodiment of the present invention.

The polarization voltage was set at −1.2 V to −1.5 V. The typical polarization Bode spectrum is shown in FIG. 9. The "A" line is without polarization and the "B" line is with −1.2 V polarization. In the polarization condition, the Zmod decreased. For example, Zmod decreased from 3.825 kΩ to 3.573 kΩ at a frequency of 500 kHz. These data suggest that the reaction is fast when the catalytic cell was polarized.

Figure 10:
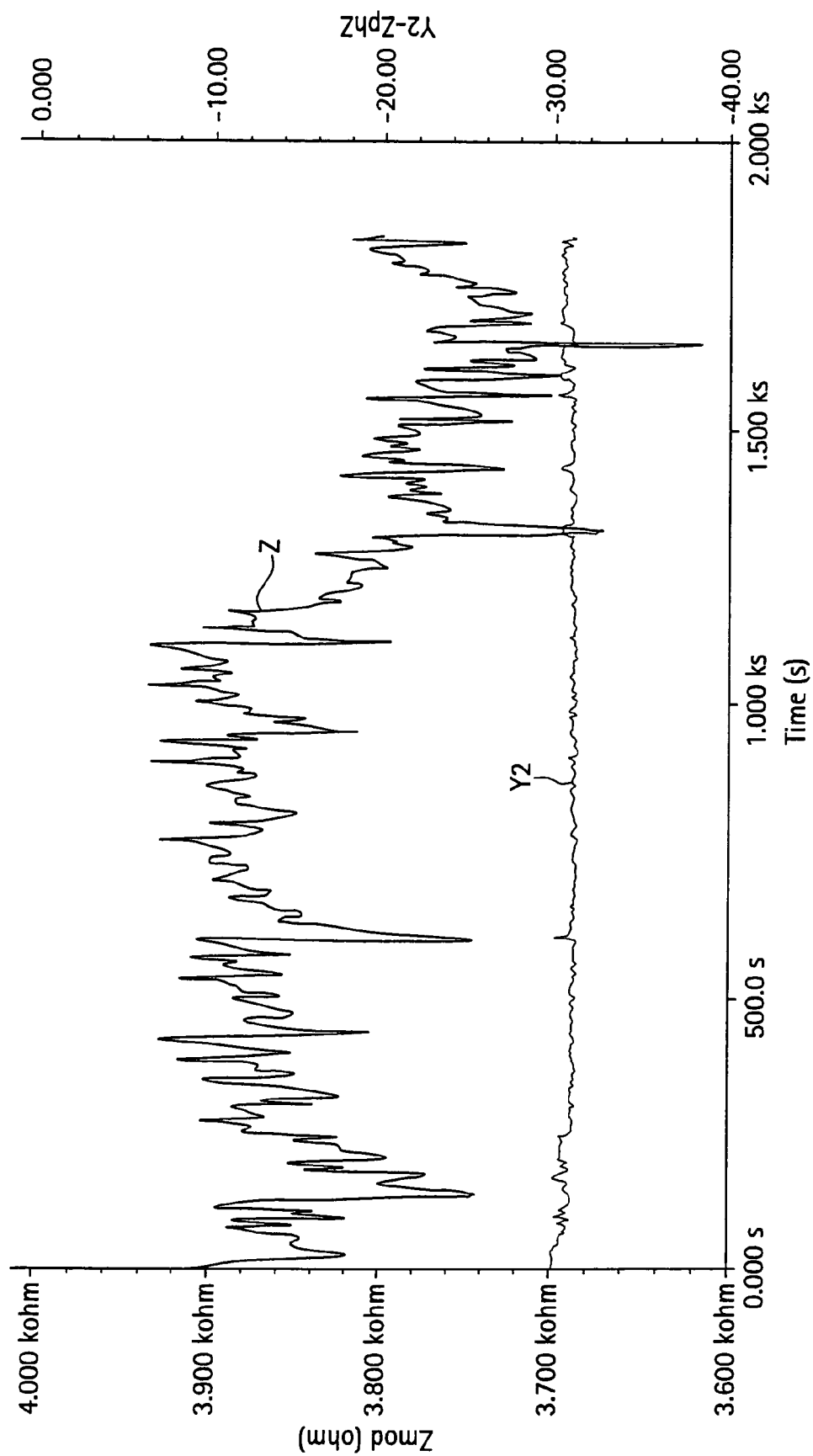
FIG. 10 shows a single frequency EIS (Electrochemical Impedance Spectroscopy) spectrum from one example embodiment of the present invention.

FIG. 10 is a single frequency EIS spectrum. With the fixed frequency of 500 KHz, the Zmod was shown to change with time. This change reflected the dynamic reactions at the surface of the catalytic assembly. The comparison tests showed that if alternating negative and positive polarizations were used, the Zmod would decrease after negative polarization, which increases the reaction rate.

Gas chromatography (GC) online analysis of the products of the reaction found new broad peaks at 14.5-20.5 min. These peaks were assigned to ethylene and ethane.

The foregoing examples are meant to illustrate the function and applicability of the present invention without limiting its scope. Those skilled in the art will appreciate that the present invention has numerous applications and that the parameters, materials, chemical compounds, products, and other variables mentioned in the examples above can be modified or changed depending on the application and desired result.

From the foregoing examples those skilled in the art will appreciate that the present invention encompasses methods, processes, and apparatus for the activation of the reaction between low-reactivity, non-polar molecules (such as $CO_2$) with polar molecules/species (such as water or steam), leading to products useful in the production of polymers, in organic synthesis reactions. For example, in accordance with the present invention a process is provided which leads to the activation of the reaction of carbon dioxide (and of other similar low-reactivity, non-polar molecules) with polar compounds (such as water, steam, or others) in a heterogeneous catalytic reaction. For example, the present invention may be used to activate the following reactions (among others):

$CO_2+H_2O$ $CO_2+H_2O+CH_4$ $CO_2+NO$ $CO_2+NO+CH_4$ $CO_2+NH_3$ $C_6H_6+H_2O$ $C_6H_6+C_6H_6+CH_4$ $C_6H_6+H_2O+CH_4$ $C_6H_6+CH_3OH$ and similar compounds $C_6H_6+NO$ $C_6H_6+NH_3$ Those skilled in the art will appreciate that the foregoing list of reactions is not intended to be limiting, and that the present invention may be used to facilitate other reactions, as discussed in detail above.

It should now be appreciated that the present invention provides advantageous methods and apparatus for the activation of carbon dioxide and other low-reactivity molecules.

Although the invention has been described in connection with various illustrated embodiments, numerous modifications and adaptations may be made thereto without departing from the spirit and scope of the invention as set forth in the claims.

What is claimed is:

1. A method for activation of a low reactivity, non-polar chemical compound, comprising:
   introducing the low reactivity chemical compound to a catalyst;
   providing at least one of (a) an oxidizing agent or a reducing agent, and (b) a polar compound to the catalyst and the chemical compound;
   applying an alternating current to said catalyst to produce an activation reaction in the chemical compound;
   wherein the activation reaction produces a useful product.

2. A method in accordance with claim 1, wherein:
   the activation reaction comprises one of a reduction or an oxidation reaction.

3. A method in accordance with claim 1, wherein:
   the polar compound comprises one of water or steam.

4. A method in accordance with claim 3, wherein:
   one of ammonia, nitric oxide, carbon monoxide, and methane are added to said water or steam.

5. A method in accordance with claim 1, wherein:
   the polar compound comprises one of water, ammonia, nitric oxide, and carbon monoxide.

6. A method in accordance with claim 1, wherein:
   the chemical compound is introduced into a chamber containing the catalyst; and
   the at least one of (a) the oxidizing agent or the reducing agent, and (b) the polar compound is introduced into the chamber.

7. A method in accordance with claim 1, wherein:
the low reactivity chemical compound comprise $CO_2$; and
the useful product comprises formaldehyde in at least one of a monomeric and a polymeric form.

8. A method in accordance with claim 1, wherein:
the low reactivity chemical compound comprises $CO_2$; and
the useful product comprises at least one of an aldehyde, trioxane, ethane, ethylene, formaldehyde, and paraformaldehyde.

9. A method in accordance with claim 1, wherein:
the useful product contains at least one of carbon, hydrogen, and oxygen.

10. A method in accordance with claim 1, wherein:
the useful product comprises at least one of an alcohol compound and an olefin.

11. A method in accordance with claim 1, wherein:
the chemical compound comprises an aromatic compound;
the providing of at least one of (a) the oxidizing agent or the reducing agent, and (b) the polar compound comprises providing the reducing agent to the catalyst and the aromatic compound.

12. A method in accordance with claim 11, wherein:
the reducing agent comprises hydrogen;
the aromatic compound comprises benzene or a benzene derivative; and
the useful product comprises cyclohexane or a benzene derivative.

13. A method in accordance with claim 1, wherein:
the chemical compound comprises an aromatic compound;
the providing of at least one of (a) the oxidizing agent or the reducing agent, and (b) the polar compound comprises providing the oxidizing agent to the catalyst and the aromatic compound.

14. A method in accordance with claim 13, wherein:
the oxidizing agent comprises oxygen; and
the aromatic compound comprises benzene or a benzene derivative.

15. A method in accordance with claim 13, wherein:
the useful product comprises at least one of acetophenone, a phenol, or a benzene derivative.

16. A method in accordance with claim 1, wherein:
the catalyst comprises one of a precious metal, a semi-conducting oxide, a semi-conducting cermet, and a varistor.

17. A method in accordance with claim 1, wherein:
the catalyst comprises one of platinum, platinum black, rhodium, rhodium black, palladium, palladium black, silver, manganese oxide, a manganese oxide derivative, molybdenum oxide, a molybdenum oxide derivative, iron oxide, an iron oxide derivative, cerium oxide, a cerium oxide derivative, titanium oxide, doped titanium oxide, cobalt oxide, rhodium oxide, and zinc oxide.

18. A method in accordance with claim 1, wherein:
the catalyst comprises a catalyst layer applied to a porous ceramic substrate.

19. A method in accordance with claim 18, wherein:
the catalyst layer is supported by a layer of a solid electrolyte.

20. A method in accordance with claim 19, wherein:
the solid electrolyte layer is one of a continuous layer or a discontinuous layer.

21. A method in accordance with claim 19, wherein:
the solid electrolyte comprises one of stabilized zirconia, Nafion, a hydrogen ion conducting material, and beta aluminas.

22. A method in accordance with claim 19, wherein:
the alternating current is applied across a three-phase boundary at an interface between the catalyst and the solid electrolyte layer.

23. A method in accordance with claim 22, wherein, for the applying of the alternating current to the catalyst layer:
a reference electrode is applied to said solid electrolyte layer;
a counter electrode is applied between the catalyst and the solid electrolyte layer; and
a working electrode is applied to the catalyst layer.

24. A method in accordance with claim 19, further comprising:
monitoring a polarization impedance of the supported catalyst layer; and
controlling the polarization impedance by varying the alternating current.

25. A method in accordance with claim 19, further comprising:
providing a controlled oxygen partial pressure environment at a level of the supported catalyst layer.

26. A method in accordance with claim 25, further comprising:
monitoring the partial pressure of the oxygen at a level of the catalyst layer.

27. A method in accordance with claim 26, wherein:
the monitoring of the partial pressure of the oxygen comprises monitoring an interfacial impedance of the supported catalyst layer; and
determining the partial pressure of oxygen at a level of the catalyst layer as a function of the interfacial impedance.

28. A method in accordance with claim 26, further comprising:
monitoring a polarization impedance of the supported catalyst layer;
wherein the partial pressure of oxygen at the level of the catalyst layer is determined as a function of the monitored polarization impedance.

29. A method in accordance with claim 19, further comprising:
monitoring a polarization impedance of the supported catalyst layer;
wherein a momentary value of the alternating current may be determined as a function of the monitored polarization impedance.

30. A method in accordance with claim 1, further comprising:
controlling an amount of the at least one of (a) the oxidizing agent or the reducing agent, and (b) the polar compound provided in order to optimize the activation reaction.

31. A method in accordance with claim 1, wherein:
controlling a ratio of an amount of the chemical compound to an amount of the at least one of (a) the oxidizing agent or the reducing agent, and (b) the polar compound provided in order to optimize the activation reaction.

32. A method in accordance with claim 1, further comprising:
applying heat to the catalyst.

33. A method for activation of a chemical compound, comprising:
introducing the chemical compound to a catalyst;
providing an oxidizing agent or a reducing agent to the catalyst and the chemical compound;
applying an alternating current to said catalyst to produce an activation reaction in the chemical compound;
wherein the activation reaction produces a useful product.

34. Apparatus for activation of a low reactivity, non-polar chemical compound, comprising:
- a catalyst;
- a means for introducing the low reactivity chemical compound to the catalyst;
- a means for providing at least one of (a) an oxidizing agent or a reducing agent, and (b) a polar compound to the catalyst and the chemical compound; and
- electrodes for applying an alternating current to the catalyst to produce an activation reaction in the chemical compound;
- wherein the activation reaction produces a useful product.

* * * * *